United States Patent
Woodward

(10) Patent No.: US 6,579,724 B2
(45) Date of Patent: Jun. 17, 2003

(54) DISPENSING METHOD AND APPARATUS FOR DISPENSING VERY SMALL QUANTITIES OF FLUID

(75) Inventor: Roger P. Woodward, Portsmouth, VA (US)

(73) Assignee: First Ten Angstroms, Portsmouth, VA (US)

( * ) Notice: Subject to any disclaimer, the term of this patent is extended or adjusted under 35 U.S.C. 154(b) by 27 days.

(21) Appl. No.: 09/950,700

(22) Filed: Sep. 13, 2001

(65) Prior Publication Data

US 2003/0049861 A1 Mar. 13, 2003

(51) Int. Cl.$^7$ .................................................. B01L 3/02
(52) U.S. Cl. ...................... 436/180; 73/864.11; 422/66; 422/100; 436/44; 436/54
(58) Field of Search ........................... 436/180, 44, 54; 422/100, 66; 73/864.11

(56) References Cited

U.S. PATENT DOCUMENTS

| | | | | |
|---|---|---|---|---|
| 5,312,757 A | * | 5/1994 | Matsuyama et al. | 436/54 |
| 5,555,767 A | * | 9/1996 | Makino et al. | 73/863 |
| 5,811,306 A | * | 9/1998 | Komatsu | 436/54 |
| 5,856,200 A | * | 1/1999 | Krause et al. | 436/180 |
| 6,083,762 A | * | 7/2000 | Papen et al. | 436/180 |
| 6,405,609 B1 | * | 6/2002 | Richards et al. | 73/864.14 |
| 6,484,556 B1 | * | 11/2002 | Jabobs et al. | 73/1.74 |

* cited by examiner

Primary Examiner—Jan Ludlow
(74) Attorney, Agent, or Firm—Whitham, Curtis & Christofferson, PC

(57) ABSTRACT

A fluid dispensing system and method includes a pump to aspirate and expel sample fluid, a fluid dispensing tip, and a metering station. The fluid dispensing tip includes a working fluid and an air gap where the air gap separates the working fluid from the sample fluid. The metering station receives a drop of sample fluid that is at least twice as large as the predetermined volume to ultimately be dispensed. The fluid dispensing tip then withdraws the predetermined volume of fluid from the sample fluid. Precise volumes are ascertained by prior knowledge of the geometry of the fluid dispensing tip and by using an imaging device to monitor an interface of either the sample fluid or working fluid with the air gap within the fluid dispensing tip. The system and method are capable of accurately dispensing very small volumes of sample fluid on the order of 10 picoliters. In addition, the system and method do not require large volumes of sample fluid to prime a pump mechanism.

8 Claims, 4 Drawing Sheets

DISPENSING METHOD AND APPARATUS FOR DISPENSING VERY SMALL QUANTITIES OF FLUID

BACKGROUND OF THE INVENTION

1. Field of the Invention

The invention pertains to methods and dispensing apparatuses providing precise, very small quantities of fluids.

2. Description of the Prior Art

It is important in a variety of industries, such as medical diagnostics, biotechnology, and scientific instrumentation, to accurately dispense very small drops of fluids. Furthermore, it is desirable to be able to program the volume of the drops so that the amount delivered will be precise and accurate while at the same time minimizing the amount of a sample required for the dispenser. Some examples of small volume dispensing devices are described in U.S. Pat. Nos. 5,366,896; 5,919,706; 5,927,547; 5,958,342; 5,998,218; 6,083,762; 6,090,348; and 6,100,094. Ink jet printer devices represent an example of a technology area where systems and methods for dispensing small volumes of fluid have been developed. However, the ink jet printer devices suffer from the drawback that they often require several microliters of fluid to prime the dispenser passage; even if only sub-nanoliter sized droplets are dispensed. In many technologies, it would be advantageous to be able to aspirate a volume of about a nanoliter or less without needing to pick up larger amounts. This problem is especially acute in forensic sciences and in biotechnology where only limited quantities of sample are available.

One difficulty with dispensing small volumes of fluid is the necessity of a tip with a small radius. The small radius results in large internal pressures that prevent the fluid from flowing easily from the tip. To overcome this limitation, other systems expel fluids by forcibly ejecting the droplets at a high velocity. However, these systems suffer from accuracy problems. It would be desirable for a system to be able to aspirate and deliver small volumes without being susceptible to clogging, while still maintaining a high level of accuracy.

SUMMARY OF THE INVENTION

It is an object of this invention to overcome the limitations of the prior art, and to provide a highly accurate dispensing device and method which allows dispensing controllable droplets of sub nanoliter size without requiring relatively large priming volumes.

This invention contemplates the use of a pipette or probe that includes a working fluid, an air gap, and a sample fluid in the dispensing tip.

The pipette or probe is used to first retrieve a quantity of the sample fluid at the tip. In the retrieval, the working fluid and air gap rise within the pipette or probe, and the sample fluid fills the end of the tip. Then, the invention contemplates dispensing a sessile drop onto a substrate. A small portion of the sample remains in the end of the tip, and the tip contacts the outer periphery of the sessile drop. A camera or other imaging device is used to measure the diameter and height of the fluid. This information is then used to calculate the volume inside the tip while it is still in contact with the sessile drop. Then, precise amounts of fluid in selectively variable quantities are drawn back up into the pipette tip from the sessile drop. The tip is then moved to a desired dispensing location, and the desired sample fluid is expelled from that remaining in the tip.

Physically, movement of fluid into a very narrow channel pipette or probe tip is difficult to achieve. The technique utilized in this invention promotes the ability to siphon up sample fluid by different mechanisms. First, creating a sessile drop physically provides a fluid with a surface of curvature that will promote siphoning. Laplace's rule states that the pressure across an interface is proportional to interfacial (surface) tension and inversely proportional to radius of curvature. The small radii inside pipette tips, therefore, leads to large pressures. Second, the liquid surface does not move smoothly over the pipette inside surface because the surface is not energetically constant (i.e., even) and because of what is known as contact angle hysteresis (advancing angles are not equivalent to receding angles). For these reasons, fluid motion is not steady; rather it is stop and start, and may often be referred to as stick/slip. Combined with the high and variable pressures from LaPlace's rule, it is extremely difficult to directly draw or dispense a specific amount from a continuum of liquid. This invention contemplates providing vibrations to the pipette or probe tip. This can be achieved by acoustic or mechanical means (e.g., a piezo ceramic element may be driven to sequentially compress and de-compress the working fluid). The larger radius of the sessile drop used in this invention lowers the pressures, and the high frequency vibrations contemplated by this invention breaks loose the stick/slip motion.

The method and apparatus of this invention are adaptable to robotic placement of very small fluid samples at precise locations. This may have application in certain antibody and DNA detection chips, as well as in a variety of other applications. For example, by having precise quantities of fluid containing an antigen or antibody or single stranded DNA or any other molecular entity placed on a chip or other substrate, it would be possible to optically assess weight differentials which are the result of selective bonding or hybridizing reactions.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
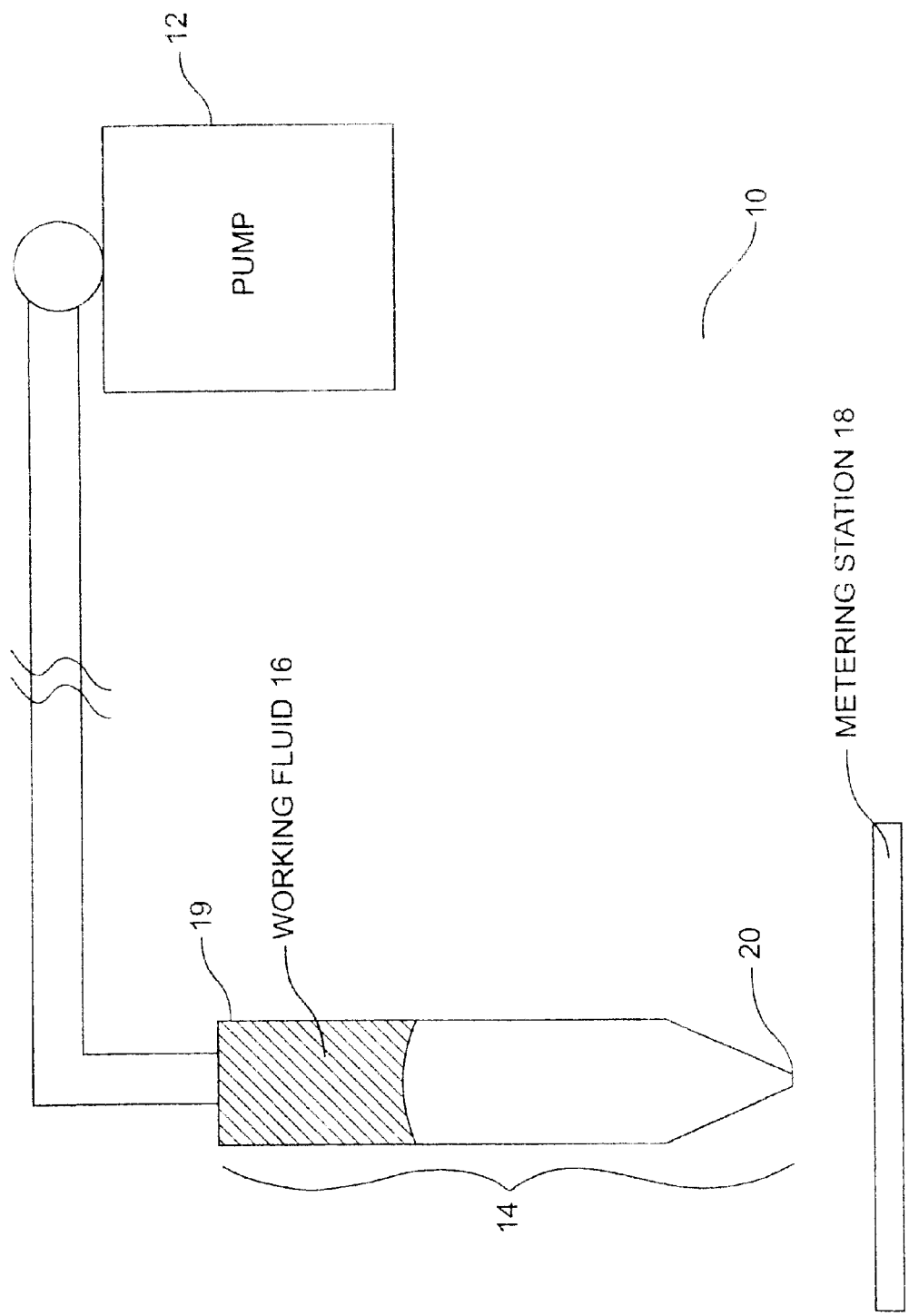
FIG. 1 is a schematic view of a fluid dispensing system embodying the invention.

As illustrated in FIG. 1, the main components of the system 10 include a pump 12, a fluid dispensing tip 14, a working fluid 16, and a metering station 18. The pump 12 functions as a mechanical displacement pump for the purpose of aspirating and dispensing fluid through fluid dispensing tip 14. The resolution of the pump 12 can vary according to the desired size of dispensed droplets. Preferably, the pump 12 is adapted to aspirate volumes on the order of 100 nanoliters or one microliter, but can also aspirate volumes as small as on the order of 10 picoliters. Suitable pumps may include piezo-electric driven diaphragm pumps, such as the FTA 4000 available from First Ten Angstroms of Portsmouth, Va.

The fluid dispensing tip 14 is used to dispense specified volumes of fluid. Preferably, the tip. 14 is adapted to dispense droplets on the order of 10 picoliters. The inner diameter of the base 19 of the tip 14 can range from about 100 μm to 1000 μm, but it is preferably 400 μm. Preferably the tip 14 is conical in shape and is narrower at the end 20 with an inner diameter ranging from about 2 μm to 20 μm. One advantage of having a tip 14 with a wider base 19 is the improved ability of the pump 12 to adjust the level of the fluids within the tip 14. The conical shape minimizes viscosity induced pressures because most of the tube is relatively large, it also accommodates a large range of volumes within the field of view of the camera (imaging device 40) used in the practice of this invention. The tip 14 is preferably transparent for inspection purposes. Inspection may be performed by an. imaging device 40 such as a video recorder or visually by an operator or by automatic computer analysis. The tip 14 may be made of any material that is not adversely affected by the fluid to be dispensed. Preferred materials include plastic and glass. Some examples of preferred embodiments include a drawn glass capillary or a fused silica fine bore tube.

A working fluid 16 is contained in the base 19 of the fluid dispensing tip 14. The working fluid 16 may be any fluid that will neither damage the pump 12 nor affect the measurement of the fluid to be dispensed. The working fluid 16 may be the same as the fluid that is to be dispensed. Preferably the working fluid is water. An air gap will always separate the working fluid from the sample.

The metering station 18 is an inert surface that is adapted to receive a drop of the dispensed fluid. The inert surface is defined to be a material that will neither absorb nor significantly react physically or chemically with the fluid to be dispensed. Preferably, the metering station 18 is made of a material that will cause the dispensed fluid to bead on the surface of the metering station 18 (e.g., the metering station 18 may be hydrophobic if the fluid to be dispensed is water-based). The preferred example of a metering station 18 is a polytetrafluoroethylene (PTFE commonly referred to as Teflon®). The size of the metering station 18 may vary as long as the metering station 18 is large enough to receive a drop of the fluid to be dispensed.

Figure 2:
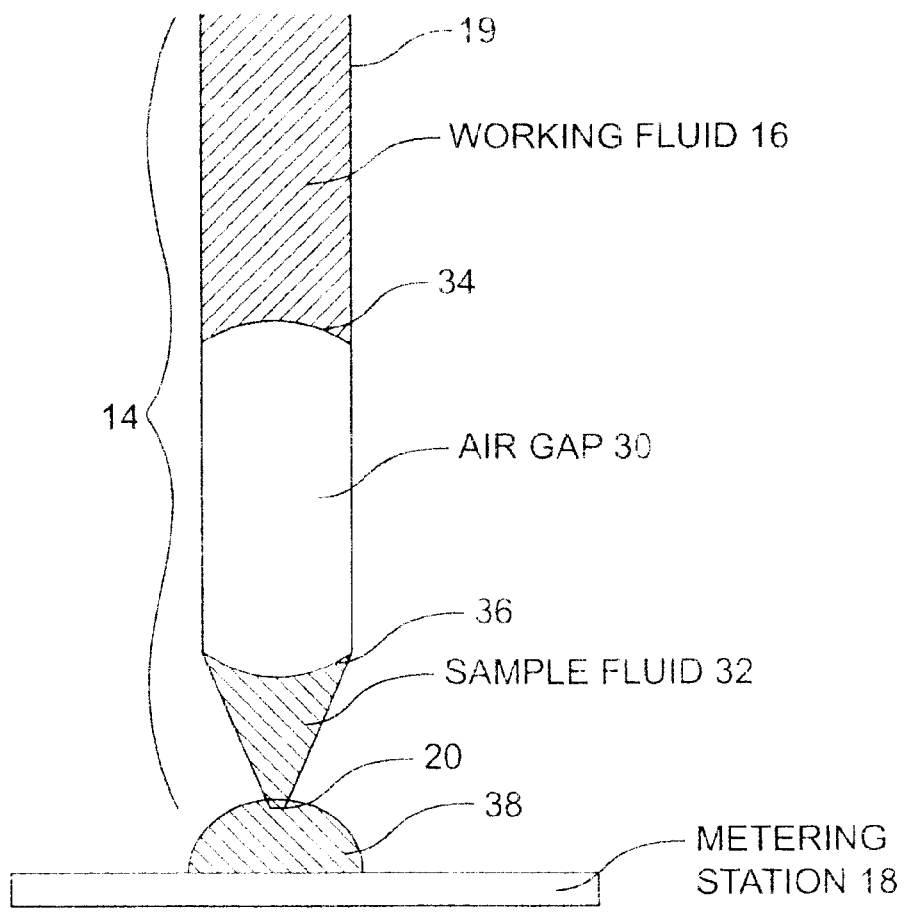
FIG. 2 is a schematic view of the tip depositing a drop of sample fluid onto the metering station.

The pump 12 controls the level of the working fluid 16 in the fluid dispensing tip 14. The portion of the tip 14 that is not filled with working fluid 16 is left filled with air. When the system 10 retrieves sample fluid 32 from a supply and aspirates it into the tip, this air becomes an air gap 30 between the working fluid 16 and the sample fluid 32 as shown in FIG. 2. The function of the air gap 30 is to clearly shown the interface 34 between the working fluid 16 and the air gap 30 and/or the interface 36 between the sample fluid 32 and the air gap 30. The air gap may be any volume but preferably ranges from 100 picoliters to 10 nanoliters. With some sample fluids, it may be desirable to use inert atmospheres such as nitrogen; therefore, within the practice of this invention it should be understood that the air gap 30 can include air, nitrogen, or any other gas.

The amount of sample fluid aspirated is controlled by the pump 12. Preferably, the pump 12 aspirates an initial quantity of sample fluid 32 from which the final amount dispensed will be taken. The fluid dispensing tip 14 is then placed close to the surface of the metering station 18. Preferably, the end 20 of the tip 14 is within a few microns of the metering station 18. A portion of the sample fluid 32 is dispensed as a sessile drop 38 onto the metering station 18. Preferably, as the sessile drop 38 is formed, it comes into contact with both the metering station 18 and the fluid dispensing tip 14.

The sessile drop 38 may have a volume ranging from 10 picoliters to 10 nanoliters. Preferably the sessile drop 38 has a volume of at least twice the ultimately desired dispense volume. Larger volumes lower pressure because of their larger radii of curvature. Preferably the sessile drop 38 is larger than the inner diameter of the end 20 of the tip 14 so that the internal pressure is lowered. Preferably, the sessile drop 38 has a radius of curvature of equal to or greater than 100 μm.

Figure 3:
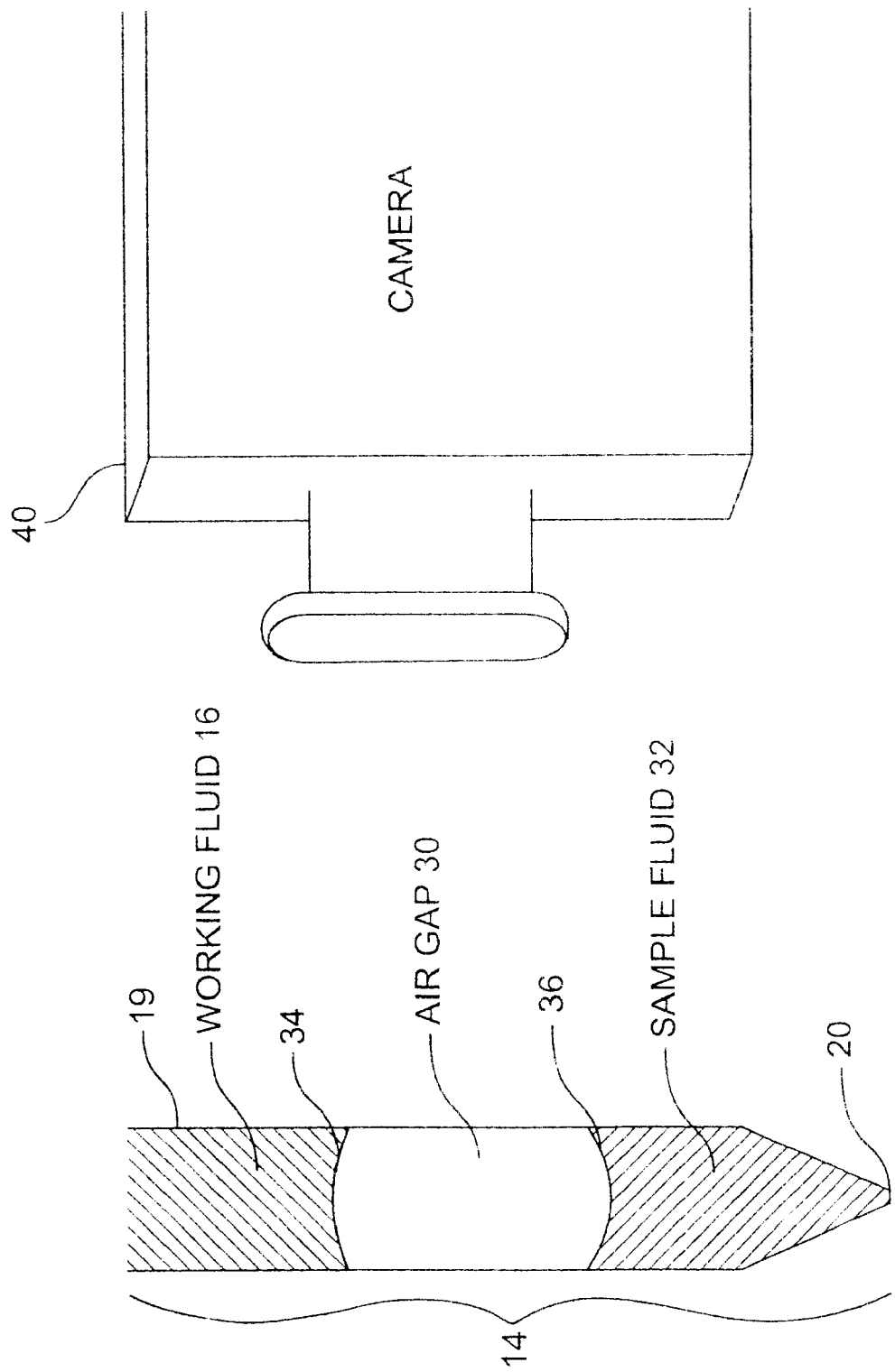
FIG. 3 is a schematic view of the tip and a camera embodying an imaging device.
Figure 4:
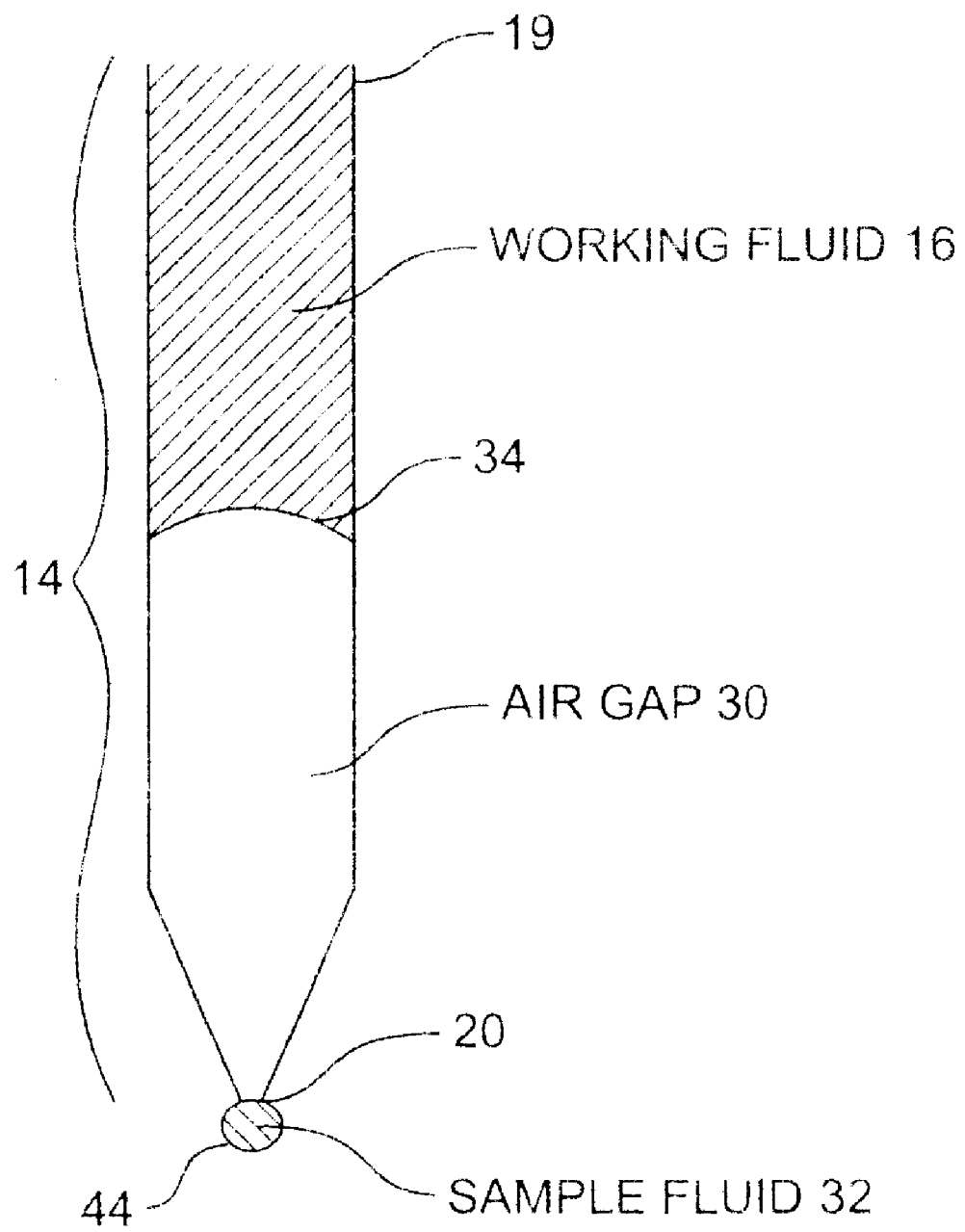
FIG. 4 is a schematic view of the tip with a hanging drop of sample fluid.

The pump 12 causes a portion of the sample fluid 32 in the sessile drop 38 to be re-aspirated into the tip 14. The volume of the sample fluid 32 in the tip 14 can be adjusted until it is the desired amount to be dispensed. Because of the practical nature of moving liquid surfaces very small distances within the pipette, it is often necessary to repetitively move back and forth and iterate to the desired volume in the tip. Preferably, the system can be used to dispense volumes of sample fluid 32 on the order of 1–100 picoliters, e.g., 10–25 picoliters, 25–75 picoliters, 50–100 picoliters, etc. The volume of sample fluid dispensed may be as small as 1 picoliter and as large as 10 nanoliters. The volume of the sample fluid is verified by visual inspection. As illustrated in FIG. 3, an imaging device 40 may be used to visually observe the interface 34 between the air gap and the working fluid 16 or alternatively the interface 36 between the air gap 30 and the sample fluid 32. The function of the imaging device 40, and associated computer software (not shown), is to assess the quantity of the sample fluid 32 being drawn into the tip 14 and ultimately being dispensed from the tip 14. Many conventional imaging devices and software analysis tools are available, e.g., charge coupled display (CCD) cameras, etc.

Once the correct volume of sample fluid 32 is contained in or at the tip 14, the tip 14 is withdrawn from the sessile drop 38. The tip 14 is then moved to a location where the sample fluid 32 is to be dispensed.. The sample fluid 32 is then expelled at this location. For very small volumes of fluid, there are evaporation problems if the fluid is hanging from the tip end.

For example, picoliters of water can evaporate in seconds. Thus, for these very small volumes (on the order of 10 picoliters) this invention takes advantage of knowing the geometry of the tip inside ahead of time (a priori). This allows relating the height of the sample in the tip ultimately to the dispensed volume. By adjusting the liquid at the metering station, a correct volume, is obtained (this may take 10 or more up and down cycles). Then all of the sample left in the tip is dispensed. This can be achieved by pumping action. Vibratory stimulation can also be used in conjunction with pumping for the same stick/slip reasons discussed above for aspiration. This allows a precise volume to be dispensed since sample fluid does not evaporate while inside-the tip.

For larger volumes, e.g., nanoliter quantities, a hanging drop methodology can be used where the imaging device 40 (or a second imaging device not shown) can be used to analyze the size of the drop formed on the tip end 20. This can be done by assessing the height and diameter of the drop. The hanging drop 44 is then touched on the surface of the dispensing location, at which point the hanging drop 44 detaches from the end 20 onto the desired location.

While the invention has been described in terms of its preferred embodiments. Those skilled in the art will recognize that the invention can be practiced with modification within the spirit and scope of the appended claims.

I claim:

1. A method for dispensing specified volumes of fluid, comprising the steps of:

aspirating a sample fluid into a fluid dispensing tip which contains a working fluid, said aspirating step being performed such that said working fluid and said sample fluid are separated by an air gap;

dispensing a first volume of said sample fluid onto a metering station surface to form a drop on said metering station surface;

aspirating a portion of said drop from said metering station surface into said fluid dispensing tip, said portion constituting a second volume of said sample fluid which is smaller than said first volume, and dispensing said portion from said fluid dispensing tip.

2. The method of claim 1 wherein said first volume of said sample fluid dispensed in said first dispensing step is at least twice as large as the second volume of said sample fluid aspirated in said second aspirating step.

3. The method of claim 1 further comprising the step of applying vibrations to said fluid dispensing tip during at least one of said two aspirating steps and said two dispensing steps.

4. The method of claim 1 wherein said second aspirating step includes iteratively applying suction and expelling fluid from said fluid dispensing tip until a desired second volume of sample fluid is positioned within said fluid dispensing tip.

5. The method of claim 1 wherein said second volume of sample fluid ranges from 1 picoliter to 10 nanoliters.

6. The method of claim 5 wherein said second volume of sample fluid is on the order of 10 picoliters.

7. The method of claim 1 further comprising the step of imaging an interface between said air gap and said working fluid.

8. The method of claim 1 further comprising the step of imaging an interface between said air gap and said sample fluid.

* * * * *